(12) United States Patent
Bonne et al.

(10) Patent No.: US 7,578,167 B2
(45) Date of Patent: Aug. 25, 2009

(54) THREE-WAFER CHANNEL STRUCTURE FOR A FLUID ANALYZER

(75) Inventors: Ulrich Bonne, Hopkins, MN (US); Robert Higashi, Shorewood, MN (US)

(73) Assignee: Honeywell International Inc., Morristown, NJ (US)

( * ) Notice: Subject to any disclaimer, the term of this patent is extended or adjusted under 35 U.S.C. 154(b) by 283 days.

(21) Appl. No.: 11/383,738

(22) Filed: May 16, 2006

(65) Prior Publication Data
US 2007/0028670 A1 Feb. 8, 2007

Related U.S. Application Data

(60) Provisional application No. 60/681,776, filed on May 17, 2005, provisional application No. 60/743,486, filed on Mar. 15, 2006.

(51) Int. Cl.
G01N 25/00 (2006.01)
(52) U.S. Cl. .................................... 73/25.01; 73/35.01
(58) Field of Classification Search ............... 73/25.01, 73/25.24, 25.25, 35.05, 31.07, 863.12, 25.03, 73/31.05, 23.4, 23.35
See application file for complete search history.

(56) References Cited

U.S. PATENT DOCUMENTS

| | | | |
|---|---|---|---|
| 3,133,837 A | 5/1964 | Eidensohn |
| 3,146,616 A | 9/1964 | Loyd |
| 3,557,532 A | 1/1971 | Broerman |
| 4,043,196 A | 8/1977 | Trageser |
| 4,048,385 A | 9/1977 | Regnaut |
| 4,228,815 A | 10/1980 | Juffa et al. |
| 4,476,196 A | 10/1984 | Poeppel et al. |
| 4,476,197 A | 10/1984 | Herceg |
| 4,478,076 A | 10/1984 | Bohrer |
| 4,483,200 A | 11/1984 | Togawa et al. |
| 4,507,974 A | 4/1985 | Yelderman |

(Continued)

FOREIGN PATENT DOCUMENTS

DE 2934566 3/1981

(Continued)

OTHER PUBLICATIONS

Aiello et al., "Production of Hydrogen from Chemical Hydrides Via Hydrolysis with Steam," International Journal of Hydrogen Energy, vol. 24, pp. 1123-1130, 1999.

(Continued)

*Primary Examiner*—John Fitzgerald
(74) *Attorney, Agent, or Firm*—Kris T. Fredrick

(57) ABSTRACT

A three-wafer channel or column structure for a fluid analyzer. The structure may have a support member, membrane, or support wafer containing heaters and interactive elements. The membrane may have a channel of one wafer facing the interactive element side and a space of another wafer facing the other side. The membrane may have perforations to equalize the pressures on both sides of the membrane. A detector in the membrane may have exposure to both the channel and space for good sensitivity, as the sample may be on both sides of the membrane. The wafers may be bonded with a thin film of non-flowing viscous material. Capillaries may be attached to an inlet and outlet of the channel and be parallel to an elongated dimension of the channel.

18 Claims, 10 Drawing Sheets

U.S. PATENT DOCUMENTS

| | | | |
|---|---|---|---|
| 4,576,050 A | 3/1986 | Lambert | |
| 4,596,748 A | 6/1986 | Katz et al. | |
| 4,659,559 A | 4/1987 | Struthers | |
| 4,735,082 A | 4/1988 | Kolloff | |
| 4,759,210 A | 7/1988 | Wohltjen | |
| 4,826,741 A | 5/1989 | Aldhart et al. | |
| 4,857,420 A | 8/1989 | Maricle et al. | |
| 4,876,163 A | 10/1989 | Reichner | |
| 4,909,078 A | 3/1990 | Sittler et al. | |
| 4,910,100 A | 3/1990 | Nakanishi et al. | |
| 4,935,040 A * | 6/1990 | Goedert | 73/23.22 |
| 4,944,035 A | 7/1990 | Aagardl et al. | |
| 5,031,126 A | 7/1991 | McCulloch et al. | |
| 5,044,766 A | 9/1991 | Stuart | |
| 5,056,047 A | 10/1991 | Sondergeld | |
| 5,116,495 A * | 5/1992 | Prohaska | 210/198.2 |
| 5,146,414 A | 9/1992 | McKown et al. | |
| 5,243,858 A | 9/1993 | Erskine et al. | |
| 5,248,426 A | 9/1993 | Stillian et al. | |
| 5,263,380 A | 11/1993 | Sultan et al. | |
| 5,268,302 A | 12/1993 | Rounbehler et al. | |
| 5,298,341 A | 3/1994 | Khandkar et al. | |
| 5,372,617 A | 12/1994 | Kerrebrock et al. | |
| 5,379,630 A | 1/1995 | Lacey | |
| 5,449,697 A | 9/1995 | Noaki et al. | |
| 5,463,899 A | 11/1995 | Zemel et al. | |
| 5,533,412 A * | 7/1996 | Jerman et al. | 73/861.95 |
| 5,587,520 A | 12/1996 | Rhodes | |
| 5,804,329 A | 9/1998 | Amendola | |
| 5,836,750 A | 11/1998 | Cabuz | |
| 5,851,689 A | 12/1998 | Chen | |
| 5,858,194 A * | 1/1999 | Bell | 204/601 |
| 5,861,221 A | 1/1999 | Ledjeff et al. | |
| 5,922,974 A | 7/1999 | Davison et al. | |
| 6,016,027 A | 1/2000 | DeTemple et al. | |
| 6,093,501 A | 7/2000 | Werth | |
| 6,139,384 A | 10/2000 | DeTemple et al. | |
| 6,178,811 B1 | 1/2001 | Bonne et al. | |
| 6,194,833 B1 | 2/2001 | DeTemple et al. | |
| 6,250,078 B1 | 6/2001 | Amendola et al. | |
| 6,258,263 B1 * | 7/2001 | Henderson et al. | 210/198.2 |
| 6,260,949 B1 * | 7/2001 | Smith et al. | 347/44 |
| 6,280,869 B1 | 8/2001 | Chen | |
| 6,308,553 B1 | 10/2001 | Bonne et al. | |
| 6,326,097 B1 | 12/2001 | Hockaday | |
| 6,393,894 B1 | 5/2002 | Bonne et al. | |
| 6,494,617 B1 | 12/2002 | Stokes et al. | |
| 6,541,149 B1 | 4/2003 | Maynard et al. | |
| 6,620,542 B2 | 9/2003 | Pan | |
| 6,792,794 B2 | 9/2004 | Bonne et al. | |
| 6,837,118 B2 | 1/2005 | Bonne et al. | |
| 6,981,522 B2 * | 1/2006 | O'Connor et al. | 137/803 |
| 7,000,452 B2 | 2/2006 | Bonne et al. | |
| 7,089,798 B2 * | 8/2006 | Silverbrook et al. | 73/729.2 |
| 7,118,711 B1 | 10/2006 | Koehler | 422/101 |
| 7,178,386 B1 * | 2/2007 | Gamble et al. | 73/61.57 |
| 7,273,517 B1 * | 9/2007 | Lewis et al. | 96/101 |
| 7,309,467 B2 * | 12/2007 | Chen et al. | 422/100 |
| 2001/0028973 A1 | 10/2001 | Ong et al. | |
| 2002/0068213 A1 | 6/2002 | Kaiser et al. | |
| 2002/0177031 A1 | 11/2002 | Doshi et al. | |
| 2003/0054215 A1 | 3/2003 | Doshi et al. | |
| 2003/0068264 A1 | 4/2003 | Schmidt et al. | |
| 2003/0150792 A1 | 8/2003 | Koehler et al. | |
| 2003/0225362 A1* | 12/2003 | Currie et al. | 604/20 |
| 2004/0025585 A1* | 2/2004 | Seki et al. | 73/204.26 |
| 2004/0060346 A1 | 4/2004 | Bonne et al. | |
| 2004/0224422 A1 | 11/2004 | Bonne et al. | |
| 2004/0259265 A1 | 12/2004 | Bonne | |
| 2005/0042139 A1 | 2/2005 | Bonne | |
| 2005/0063865 A1 | 3/2005 | Bonne et al. | |
| 2005/0141999 A1 | 6/2005 | Bonne | |
| 2005/0142662 A1 | 6/2005 | Bonne | |
| 2006/0081062 A1* | 4/2006 | Silverbrook et al. | 73/754 |

FOREIGN PATENT DOCUMENTS

| | | |
|---|---|---|
| DE | 3234146 | 9/1982 |
| DE | 4222458 | 1/1994 |
| DE | 4243573 | 6/1994 |
| DE | 29607315 | 8/1996 |
| DE | 19619133 | 11/1997 |
| DE | 19734259 | 2/1999 |
| EP | 0189316 | 7/1986 |
| EP | 0232719 | 8/1987 |
| EP | 0348245 | 12/1989 |
| EP | 0364982 | 4/1990 |
| EP | 0419873 | 8/1990 |
| EP | 0468793 | 1/1992 |
| EP | 0666768 | 8/1995 |
| EP | 0702212 | 3/1996 |
| EP | 0773432 | 5/1997 |
| EP | 1351329 | 10/2003 |
| EP | 1496561 | 1/2005 |
| GB | 723180 | 2/1955 |
| GB | 2287792 | 9/1995 |
| JP | 56153256 | 11/1981 |
| JP | 57131029 | 8/1982 |
| JP | 57138782 | 8/1982 |
| JP | 57206830 | 12/1982 |
| JP | 60000066 | 1/1985 |
| JP | 4342439 | 11/1992 |
| JP | 9326259 | 12/1997 |
| JP | 2004206998 | 7/2004 |
| WO | 9206369 | 4/1992 |
| WO | 9420825 | 9/1994 |
| WO | 9822793 | 5/1998 |
| WO | 0035032 | 6/2000 |
| WO | 0045457 | 8/2000 |
| WO | 0062919 | 10/2000 |
| WO | 2004025750 | 3/2004 |

OTHER PUBLICATIONS

Amendola et al., "A Novel High Power Density Borohydride-Air Cell," Electromechanical Society Proceedings, vol. 98-15, pp. 47-54, Nov. 1, 1998.

Amendola et al., "A Safe Portable Hydrogen Gas Generator Using Aqueous Borohyfride Solution and Ru Catalyst," International Journal of Hydrogen Energy, Vo., 25, No. 10, pp. 969-975, Oct. 2000.

Amendola et al., An Ultrasafe Hydrogen Generator: Aqueous, Alkaline Borohydride Solutions and RU Calalyst, Journal of Power Sources, vol. 85, No. 2, pp. 186-189, Feb. 2000.

Atalla et al., "Radiation Effects with the AC Heated Strip Technique for the Measurement of Thermal Properties of Liquids", High Temperatures—High Pressures, vol. 17, pp. 447-452, 1985.

Atalla et al. "Measurement of Thermal Properties of Liquids with an AC Heated-Wire Technique", International Journal of Thermophysics, vol. 2, No. 2, 1981.

Bonne et al., "Industrial Wireless PHASED Sensor Phase 1. Feasibility Demonstration," Progress Report for 4th Quarter of 2002, pp. 1-17, Jan. 31, 2002.

Bonne, et al., "Actuation-based Microsensors," Smart Materials and Structures, 10, pp. 1185-1195, 2001.

Bonne et al., "Micro Gas Chromatography Tradeoff Study, Final Report," 54 pages, Nov. 2003.

Bonne, et al., "PHASED, a Faster, Smarter and More Affordable Gas Analysis Device—Update," International Forum on Process Analytical Chemistry (IFPAC) Scottsdale, AZ, Jan. 21-24, 2003.

Boone, et al., "PHASED: A Faster, Smarter and More Affordable Gas Analysis Device," 16th International Forum on Process Analytical Chemistry, San Diego, CA, Jan. 22-25, 2002, pp. 1-17.

Boone, U., et al., "New Gas Composition and Trace Contaminant Sensors," GTI Natural Gas Technologies Conference, Orland, FL, Sep. 30-Oct. 2, 2002, pp. 1-12.

Cabuz, C. et al., "Mesoscopic Sampler Based on 3-DF Arrays of Electrostatically Actuated Diaphragms," Proc. 10th Conf. S.S. S&A. Transducers '99 Jun. 7-12, 1999, Sendai, Japan.

Cabuz, C., et al., "The Dual Diaphragm Pump," IEEE, pp. 519-522, 2001.

Dipl.-Ing. Dr. techn. Wolfgang Wehrmann et al., "Korrelationstechnik", Expert Verlag, Grafenau, XP002094984, 173 pages, 1980.

Fuggerth, Endre, "Zone Gas Chromatography," Analytical Chemistry, 61, No. 14, pp. 1478-1485, (1989).

Honeywell Electronic Materials Interconnect Solutions, Thin Films—Dielectrics, Comparison of Solution and Film Properties, Advanced Products for IC Fabrication, 1 pages prior to Jan. 23, 2003. http://www.advanced-polymers.com/star_center/technical_papers/reduction_in_effective_dielectric_constant.pdf, 1 page.

http://www.chrompack.com/cgi/applicsview?ap=A00607&Go=G0, NexTrieve document view, 2 pages, printed Dec. 26, 2002.

http://www.zoex.com/html/technote_kt030505-1.html, Zoex Corporation,"A New Window on the Che," 5 pages, printed Mar. 15, 2004.

International Search Report, PCT/US00/19924, mailed Mar. 5, 2001, 7 pages.

Kenndler, Ernst, "Gas Chromatography," Institute for Analytical Chemistry, University of Vienna, pp. 1-34, Sep. 9, 1999.

Kindlund et al., "Quartz Crystal Gas Monitor With Gas Concentrating Stage," Sensors and Actuators, 6 (1984) pp. 1-17.

Park, et al., "Microdischarge Arrays: A New Family of Photonic Devices (Revised)," IEEE Journal on Selected Topics in Quantum Electronics, vol. 8, No. 2, pp. 387-394, Mar./Apr. 2002.

Park, et al., "Photodetection in the visible, ultraviolet, and near-infrared with silicon microdischarge devices," Applied Physics Letters, vol. 81, No. 24, pp. 4529-4531, Dec. 9, 2002.

Park, et al., "Arrays of silicon micro discharge devices with multicomponent dielectrics," Optics Letters, vol. 26, No. 22, pp. 1773-1775, Nov. 15, 2001.

Phillips, J.B. et al., "Thermal Modulation: A Chemical Instrumentation Component of Potential Value in Improving Portability," Field Analytical Chemistry and Technology, 1(1): 23-29, 1996.

Quimby, et al., "Evaluation of a Microwave Cavity, Discharge Tube, and Gas Flow System of Combined Aas Chromatography—Atomic Emission Detection," Analytical Chemistry, vol. 62, No. 10, pp. 1027-1034, May 15, 1990.

Stevenson, Robert, "Wintergreen '97," The World of Separation Science, The 19th International Symposium on Capillary Chromatography and Electrophoresis, 11 pages., printed Jul. 22, 2003.

Tiggelaar et al., "Analysis Systems for the Detection of Ammonia Based on Micromachined Components Modular Hybrid Versus Monolithic Integrated Approach," Elsevier Science B.V., 2003.

Toker et al., "Design and development of a fiber optic TDI CCD-based slot-scan digital mammography system," X-ray Detector Physics and Applications II, Proceedings SPIE-The International Society for Optical Engineering, vol. 2009 pp. 246-252, Jul. 13-14, 1993.

Whitman et al.,"Double-Injection FIA Using First-Order Calibration for Multicomponent Analysis," Analytical Chemistry 63, pp. 775-781, 1991.

* cited by examiner

THREE-WAFER CHANNEL STRUCTURE FOR A FLUID ANALYZER

This application claims the benefit of U.S. Provisional Application No. 60/681,776, filed May 17, 2005. This application claims the benefit of U.S. Provisional Application No. 60/743,486, filed Mar. 15, 2006.

The U.S. Government may have some rights in the present invention.

BACKGROUND

The present invention pertains to fluid analyzer structures and particularly to micro fluid analyzers. More particularly, the invention pertains to the fluid carrying structures of the analyzers.

U.S. patent application Ser. No. 11/383,723, filed May 16, 2006, entitled "An Optical Micro-Spectrometer," by U. Bonne et al., is hereby incorporated by reference. U.S. patent application Ser. No. 11/383,728, filed May 16, 2006, entitled "Chemical Impedance Detectors for Fluid Analyzers," by U. Bonne et al., is hereby incorporated by reference. U.S. patent application Ser. No. 11/383,663, filed May 16, 2006, entitled "A Thermal Pump," by U. Bonne et al., is hereby incorporated by reference. U.S. patent application Ser. No. 11/383,650, filed May 16, 2006, entitled "Stationary Phase for a Micro Fluid Analyzer," by N. Iwamoto et al., is hereby incorporated by reference. U.S. Provisional Application No. 60/681,776, filed May 17, 2005, is hereby incorporated by reference. U.S. Provisional Application No. 60/743,486, filed Mar. 15, 2006, is hereby incorporated by reference. U.S. patent application Ser. No. 10/909,071, filed Jul. 30, 2004, is hereby incorporated by reference. U.S. Pat. No. 6,393,894, issued May 28, 2002, is hereby incorporated by reference. U.S. Pat. No. 6,837,118, issued Jan. 4, 2005, is hereby incorporated by reference. U.S. Pat. No. 7,000,452, issued Feb. 21, 2006, is hereby incorporated by reference. These applications and patents may disclose aspects of structures and processes related to fluid analyzers.

SUMMARY

The invention is a structure of the fluid carrying channel, column or capillary having gaps or openings on the membrane of the channel or the like, for an analyzer. This structure may improve the sensitivity of thermal conductivity detectors situated in such channels.

DESCRIPTION

Figure 1:
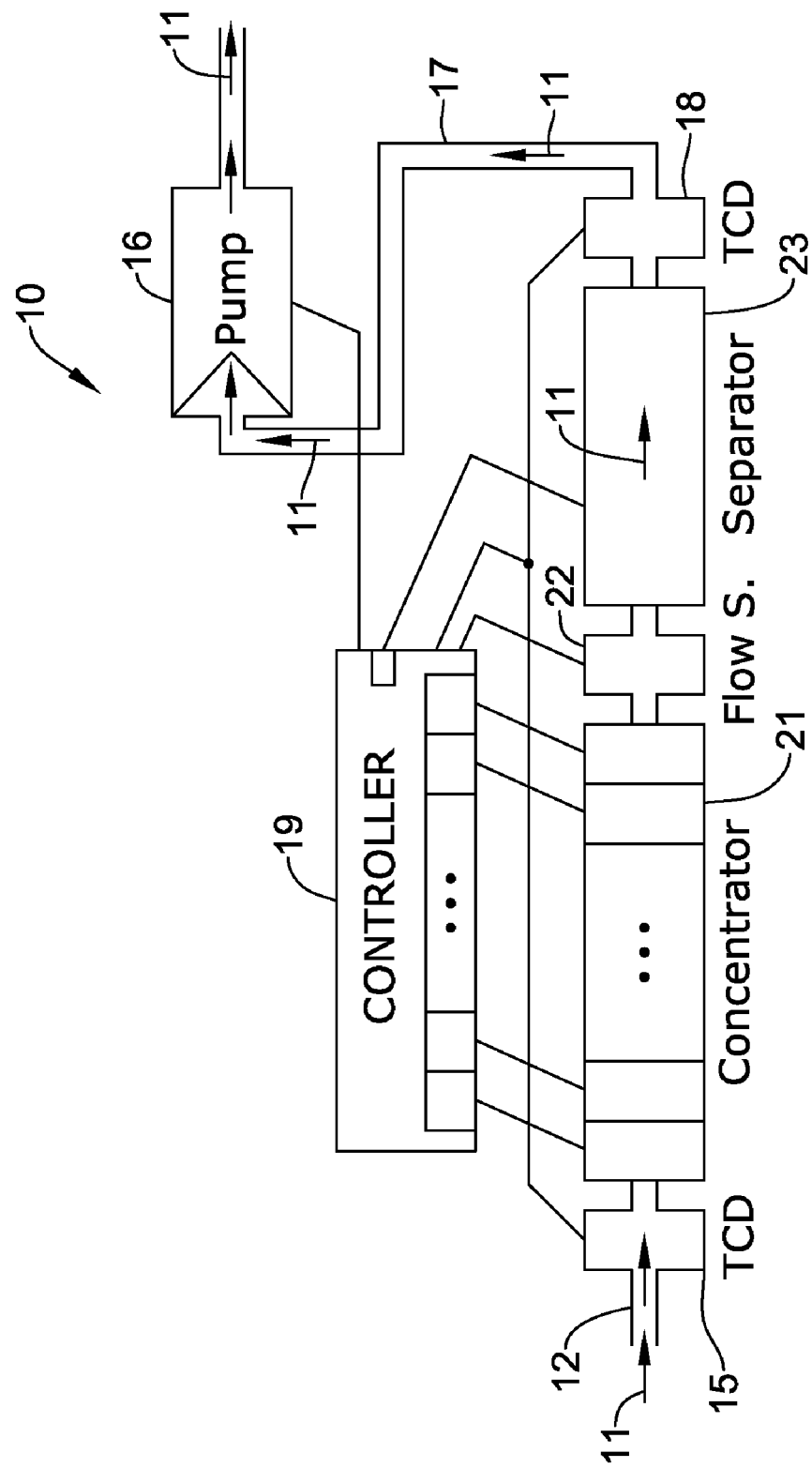
FIG. 1 is a system view of an illustrative phased heater array structure for enhanced detection fluid analyzer which may encompass the present channel and thermal conductivity detector.

The invention may include a channel or channels for a flow of a sample along a membrane that supports heaters and a stationary phase for sample analysis. The channel or channels may be an integral part of a micro fluid analyzer. The analyzer may have a pre-concentrator (PC) (viz., concentrator) and chromatographic separator (CS) that incorporates the channel or channels. FIG. 1 is a system view of the fluid analyzer which may be a phased heater array structure for enhanced detection (PHASED) micro gas analyzer (MGA) 10. It reveals certain details of the micro gas apparatus 10 which may encompass the specially designed channel described herein. The PHASED MGA 10, and variants of it, may be used for various chromatography applications.

Sample stream 11 may enter input port 12 to the first leg of a differential thermal-conductivity detector (TCD) (or other device) 15. A pump 16 may effect a flow of fluid 11 through the apparatus 10 via tube 17. The pump may be a thermal pump, or a non-thermal pump, and may be integrated in the concentrator 21 and/or separator 23, or be external to the concentrator or separator. There may be additional or fewer pumps, and various tube or plumbing arrangements or configurations for system 10 in FIG. 1. Fluid 11 may be moved through a TDC 15, concentrator 21, flow sensor 22, separator 23 and TDC 18. Controller 19 may manage the fluid flow, and the activities of concentrator 21 and separator 23. Controller 19 may be connected to TDC 15, concentrator 21, flow sensor 22, separator 23, TDC 18, and pump 16. Data from detectors 15 and 18, and sensor 22 may be sent to controller 19, which in turn may process the data. The term "fluid" may refer to a gas or a liquid, or both.

Figure 2:
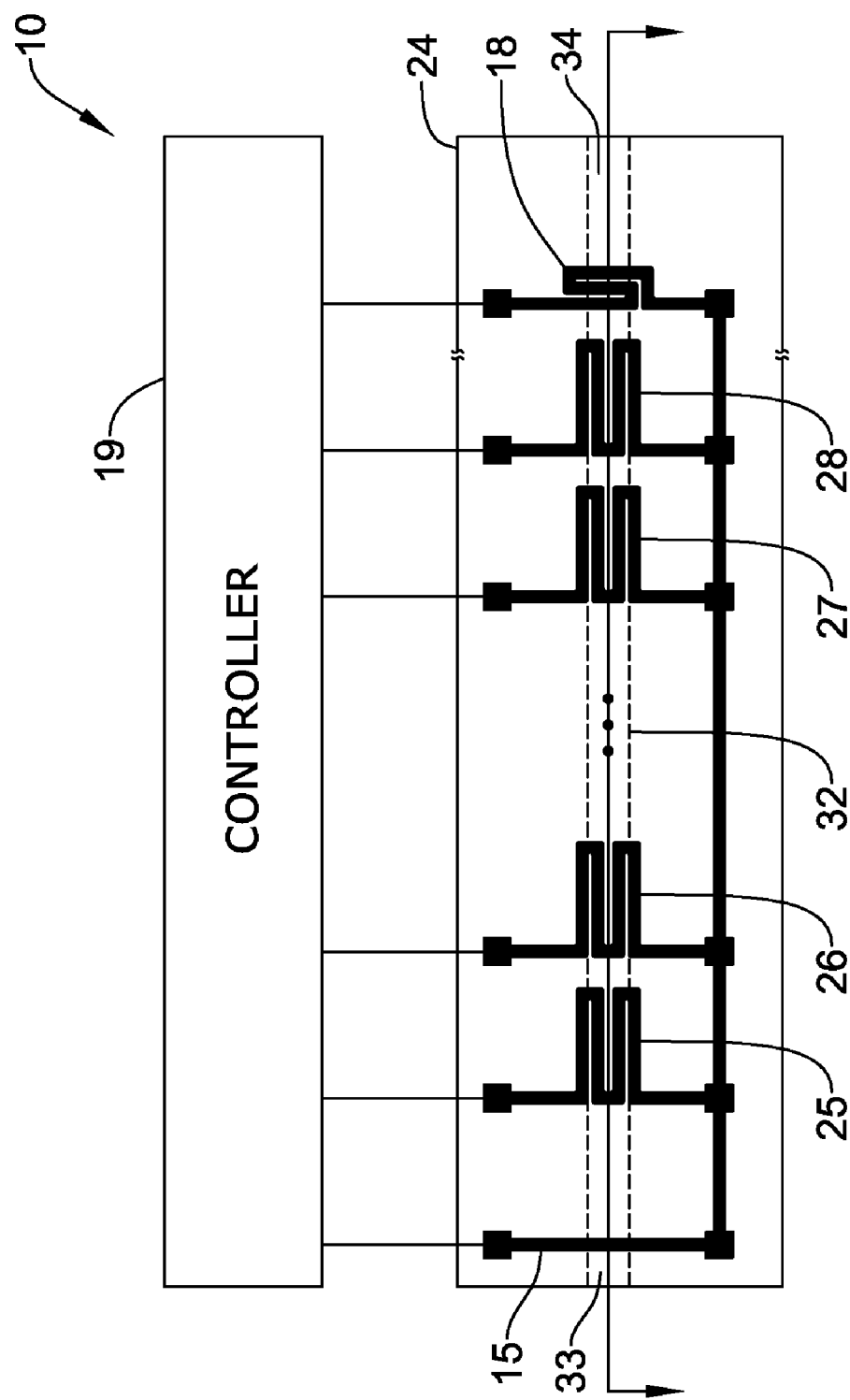
FIG. 2 shows a top view of a phased heater arrangement.

FIG. 2 is a schematic diagram of part of the sensor apparatus 10 representing a heater portion of concentrator 21 and/or separator 23 in FIG. 1. This part of sensor apparatus 10 may include a substrate or holder 24 and controller 19. Controller 19 may or may not be incorporated into substrate 24. Substrate 24 may have a number of thin film heater elements 25, 26, 27, and 28 positioned thereon. While only four heater elements are shown, any number of heater elements may be provided, for instance, between two and one thousand, but typically in the 20-100 range. Heater elements 25, 26, 27, and 28 may be fabricated of any suitable electrical conductor, stable metal, alloy film, or other material. Heater elements 25, 26, 27, and 28 may be provided on a thin, low-thermal mass, low-in-plane thermal conduction, membrane, substrate or support member 24, as shown in FIGS. 2 and 3.

Figure 3:
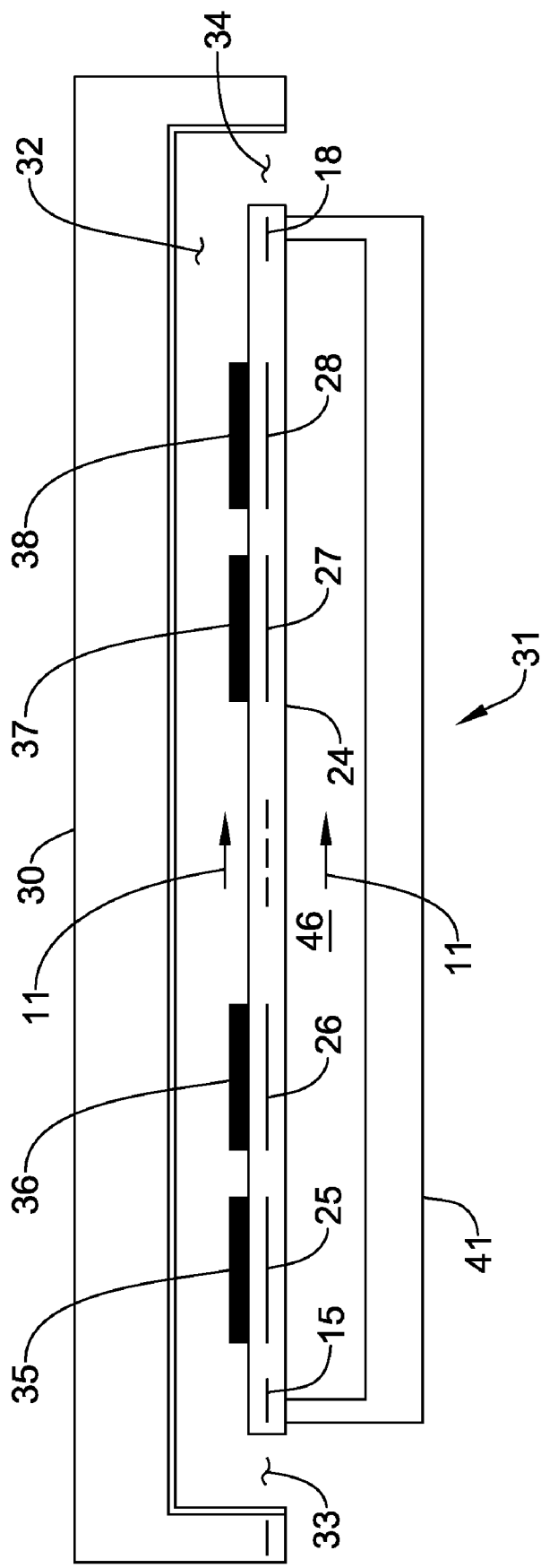
FIG. 3 is a cross section view of the heater arrangement and associated interactive elements.

In FIG. 3, substrate 30 may have a well-defined single-channel phased heater mechanism and channel structure 31 having a channel 32 for receiving the sample fluid stream 11. The channel may be fabricated by selectively etching a silicon channel wafer substrate 30 near the support member 24. The channel may include an entry port 33 and an exhaust port 34.

Figure 5A:
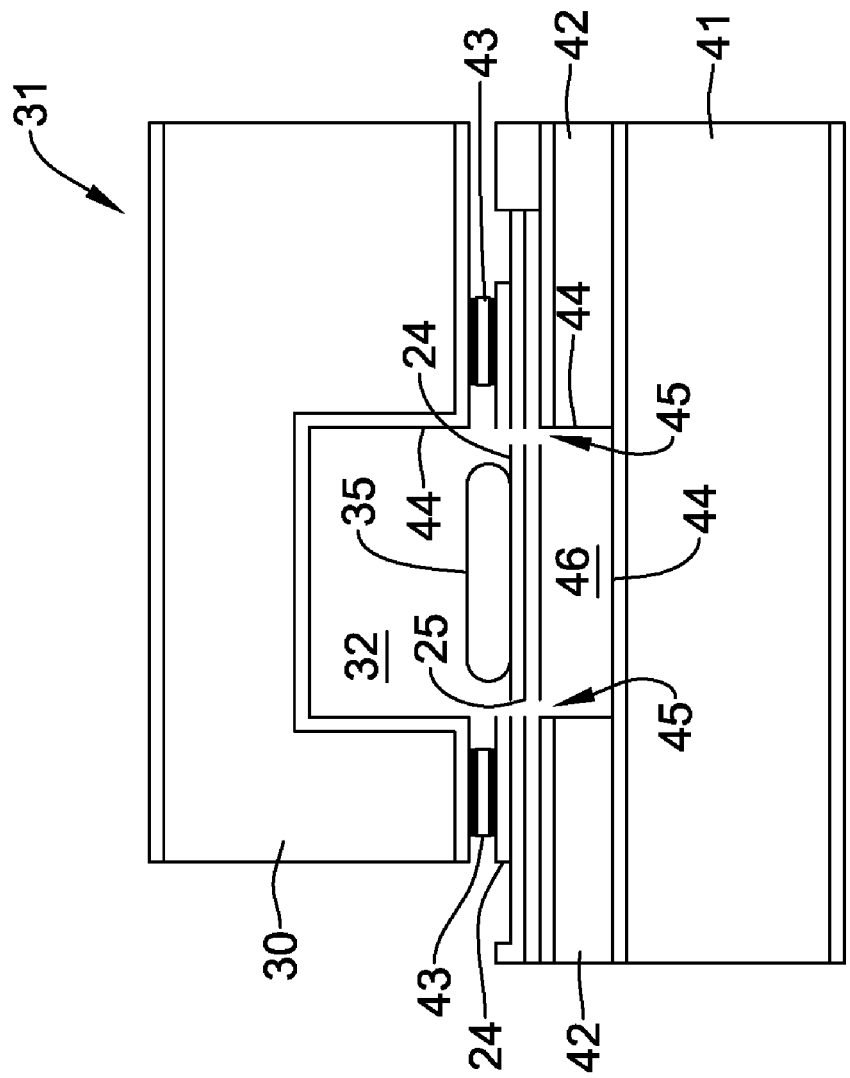
FIGS. 5a and 5b are cross-section and top views, respectively, of an illustrative example of a channel in the analyzer.
Figure 5B:
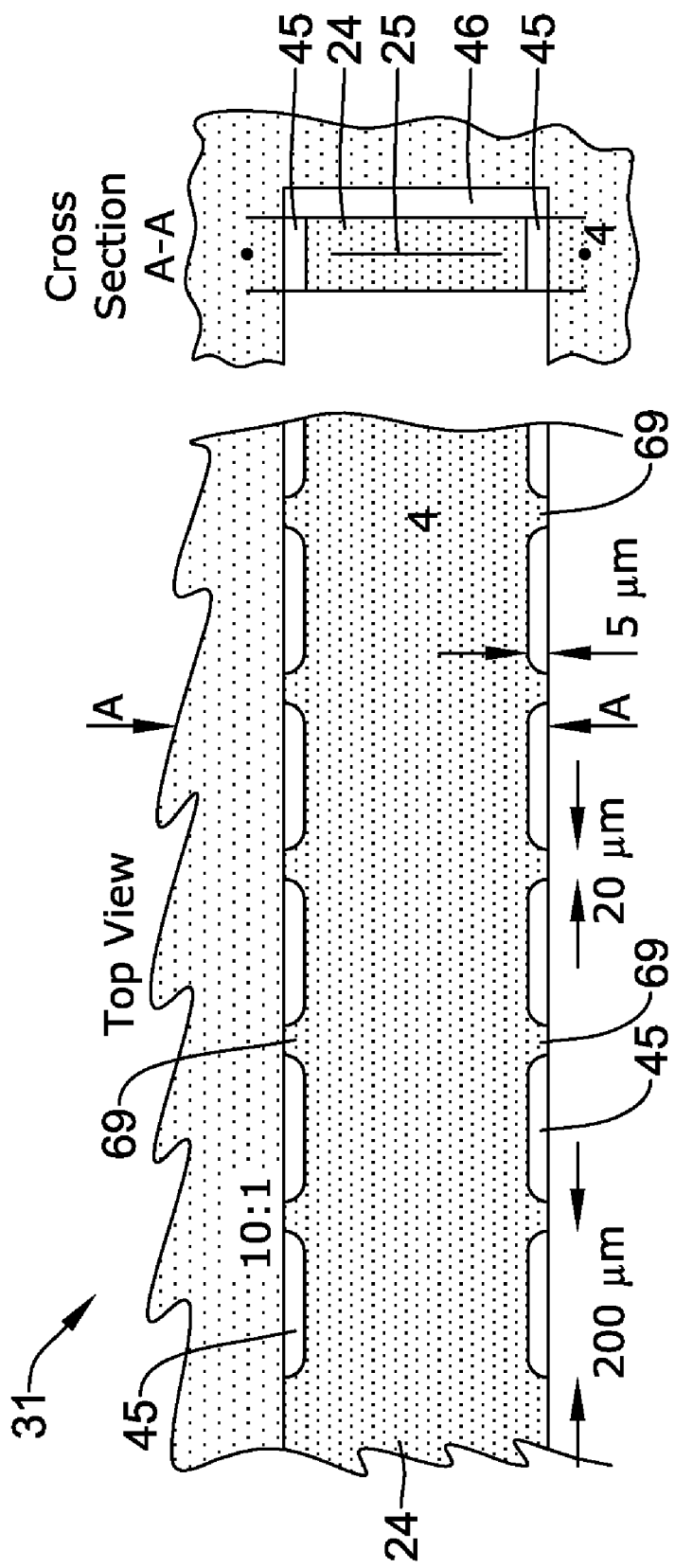
Figure 6:
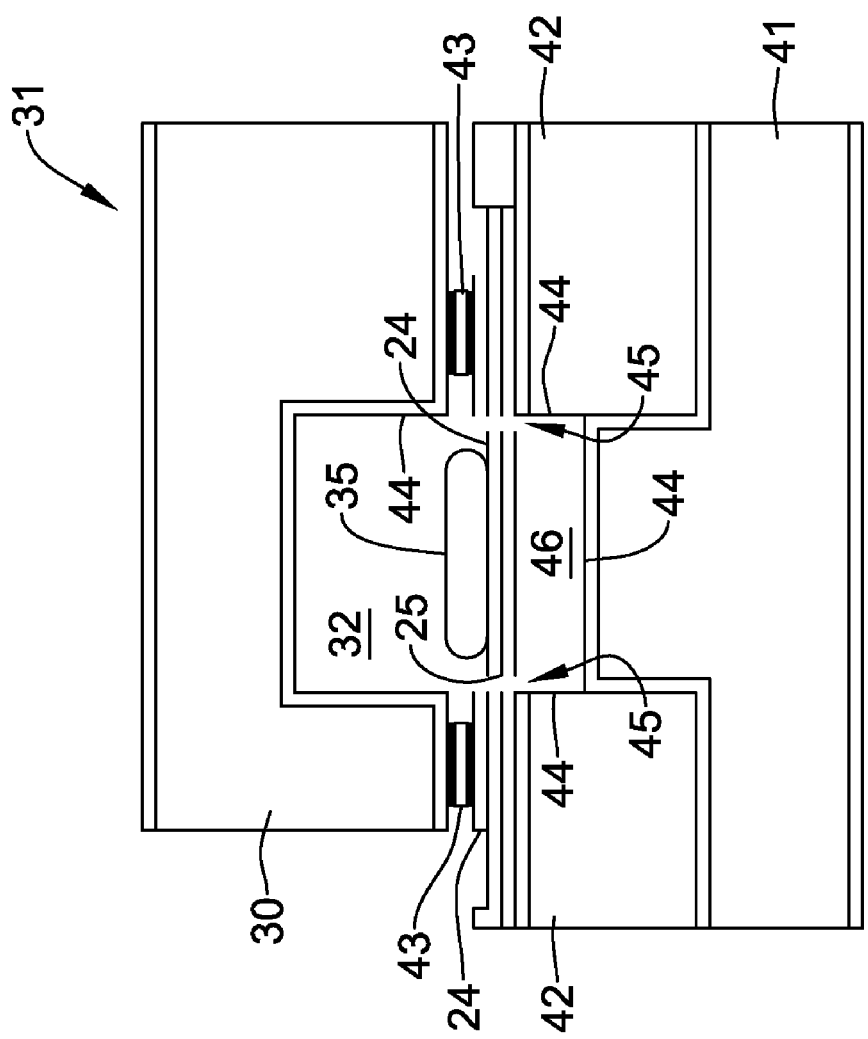
FIG. 6 is a cross-section view of another illustrative example of a channel in the analyzer.

The sensor apparatus 10 may also include a number of interactive elements inside channel 32 so that they are exposed to the streaming sample fluid 11. Each of the interactive elements may be positioned adjacent, i.e., for closest possible thermal contact, to a corresponding heater element. For example, in FIG. 3, interactive elements 35, 36, 37, and 38 may be provided on a surface of support member 24 in channel 32, and be adjacent to heater elements 25, 26, 27, and 28, respectively. There may be detectors 15 and 18 at the ends of channel 32. There may be a channel or space 46 on the other side of support member 24 through which the sample fluid 11 may also be present. The channel or space 46 may have its ends blocked by wafer or bottom cap 41, where the inlet 33 and outlet 34 are situated, such that space 46 is like a sealed containment. Entry and exit of sample 11 in channel or space 46 may be through perforations 45 in the support member or membrane 24, as shown in FIGS. 5a, 5b and 6. The structural configuration of wafer 41 and associated components of mechanism 31 may be different than those of the illustrative example shown in FIG. 3.

There may be other channels having interactive film elements which are not shown in the present illustrative example. The interactive elements may films be formed from any number of substances commonly used in liquid or gas chromatography. Furthermore, the interactive substances may be modified by suitable dopants to achieve varying degrees of polarity and/or hydrophobicity, to achieve optimal adsorption and/or separation of targeted analytes.

The micro gas analyzer 10 may have interactive elements 35, 36, . . . , 37 and 38 fabricated with various approaches, such that there is a pre-arranged pattern of concentrator and separator elements are coated with different adsorber materials A, B, C, . . . (known in gas chromatography (GC) literature as stationary phases). Not only may the ratio of concentrator 21/separator 23 elements be chosen, but also which elements are coated with A, B, C, . . . , and so forth, may be determined (and with selected desorption temperatures) to contribute to the concentration and separation process. A choice of element temperature ramping rates may be chosen for the A's which are different for the B, C, . . . , elements. Versatility may be added to this system in a way that after separating the gases from the group of "A" elements, another set of gases may be separated from the group of "B" elements, and so forth.

Controller 19 may be electrically connected to each of the heater elements 25, 26, 27, 28, and detectors 15 and 18 as shown in FIG. 2. Controller 19 may energize heater elements 25, 26, 27 and 28 in a time phased sequence (see bottom of FIG. 4) such that each of the corresponding interactive elements 35, 36, 37, and 38 become heated and desorb selected constituents into a streaming sample fluid 11 at about the time when an upstream concentration pulse, produced by one or more upstream interactive elements, reaches the interactive element. Any number of interactive elements may be used to achieve the desired concentration of constituent gases in the concentration pulse. The resulting concentration pulse may be sensed by detector 18 for analysis by controller 19.

Figure 4:
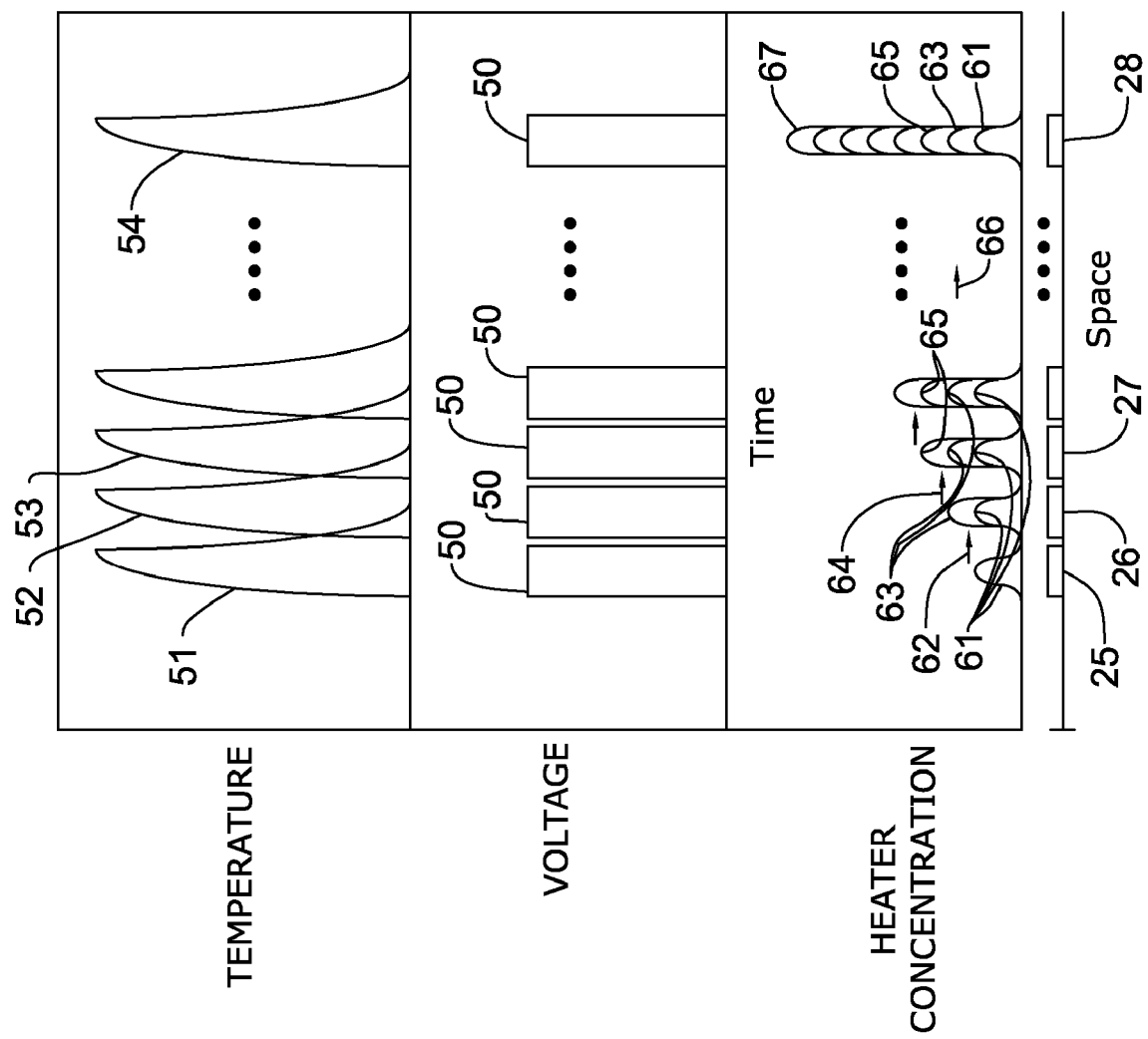
FIG. 4 shows graphs illustrating a phased heater arrangement operation.

FIG. 4 is a graph showing illustrative relative heater temperatures, along with corresponding concentration pulses produced at each heater element. As indicated herein, controller 19 may energize heater elements 25, 26, 27 and 28 in a time phased sequence with voltage signals 50. Time phased heater relative temperatures for heater elements 25, 26, 27, and 28 may be shown by temperature profiles or lines 51, 52, 53, and 54, respectively.

In the example shown, controller 19 (FIG. 2) may first energize heater element 25 to increase its temperature as shown at line 51 of FIG. 4. Since the first heater element 25 is thermally coupled to first interactive element 35 (FIG. 3), the first interactive element desorbs selected constituents into the streaming sample fluid 11 to produce a first concentration pulse 61 (FIG. 4), while no other heater elements are not yet pulsed. The streaming sample fluid 11 carries the first concentration pulse 61 downstream toward second heater element 26, as shown by arrow 62.

Controller 19 may next energize second heater element 26 to increase its temperature as shown at line 52, starting at or before the energy pulse on element 25 has been stopped.

Since second heater element 26 is thermally coupled to second interactive element 36, the second interactive element also desorbs selected constituents into streaming sample fluid 11 to produce a second concentration pulse. Controller 19 may energize second heater element 26 in such a manner that the second concentration pulse substantially overlaps first concentration pulse 61 to produce a higher concentration pulse 63, as shown in FIG. 4. The streaming sample fluid 11 may carry the larger concentration pulse 63 downstream toward third heater element 27, as shown by arrow 64.

Controller 19 may then energize third heater element 27 to increase its temperature as shown at line 53 in FIG. 4. Since third heater element 27 is thermally coupled to third interactive element 37, third interactive element 37 may desorb selected constituents into the streaming sample fluid to produce a third concentration pulse. Controller 19 may energize the third heater element 27 such that the third concentration pulse substantially overlaps the larger concentration pulse 63, provided by the first and second heater elements 25 and 26, to produce an even larger concentration pulse 65. The streaming sample fluid 11 may carry this larger concentration pulse 65 downstream toward an "Nth" heater element 28, as shown by arrow 66.

Controller 19 may then energize "N-th" heater element 28 to increase its temperature as shown at line 54. Since "N-th" heater element 28 is thermally coupled to an "N-th" interactive element 38, "N-th" interactive element 38 may desorb selected constituents into streaming sample fluid 11 to produce an "N-th" concentration pulse. Controller 19 may energize "N-th" heater element 28 in such a manner that the "N-th" concentration pulse substantially overlaps the large concentration pulse 65 as provided by the previous N−1 interactive elements, to produce a larger concentration pulse 67. The streaming sample fluid 11 may carry the resultant "N-th" concentration pulse 67 to either a separator 23 and/or a detector 18.

FIGS. 5a and 6 show cross-section end views of a phased heater mechanism 31 of analyzer 10. The channel phased heater mechanism may be incorporated in the membrane or support member 24. Support member 24 may be attached to structure, wafer or substrate 30. Anchors 43 may hold support member 30 in place, relative to structure 30 and internal channel 32. The support member 24 may be situated on a substrate or wafer 42 which may have a space, channel or opening 46 proximate to or under the support member 24 between the structure, support or wafer 41 and support member 24. There may be, on the bottom cap or wafer 41, a wafer 42 for supporting membrane or support member 24, as illustrated in FIGS. 5a and 6. FIG. 5a may represent a structure with a thinned-out (to a level equal to the desired height of the bottom channels) middle wafer that also supports the membrane with openings. FIG. 6 may accomplish the same top and bottom channels, but rather than thinning out the middle wafer, the bottom wafer has "pegs" that partially "plug" the bottom channel up to the desired height. Items 32 and 46 in FIGS. 5a and 6 may be regarded as two channels, e.g., an upper channel and lower channel.

In the structure 31, the openings in the membrane may equalize the pressures in the upper and lower (first and second) channels, and inhibit thermal conduction between a heated membrane and one or more walls of one or more channels. The structure may have a detector situated in the membrane, and the detector may have a sensing area facing the first channel and facing the second channel. At least one element of the structure of the upper wafer, the middle wafer, the lower wafer (from an orientation of the FIGS. 5a and 6) and the membrane, may have a material of lower thermal conductivity than silicon.

The structure 31 in FIG. 5a may have a bottom cap wafer 41 that has a surface which is level with the top of the wafer 42. The structure 31 in FIG. 6 may have a portion on the bottom cap wafer 41 that rises above the bottom part of space 46 of wafer 42. The aspect of minimizing space 46 may be desirable in some instances. The structure 31 in FIGS. 5a, 5b and 6 may have cutouts, perforations, or ports 45 in the membrane or support member 24 between the channels or spaces 32 and 46, so that the sample fluid may move among these channels or spaces.

A coating 44 of a non-adsorbing, thermal insulating material may be applied to the inside walls of channel 32 in the heater and sample conveyance mechanism structure 31, except where there are adsorber coated surfaces, by design, such as interactive elements or the stationary phase.

The present channel structure 31 where the fabrication of a membrane or support member 24 with cutouts 45, as illustrated in FIGS. 5a, 5b and 6, may have numerous advantages, including its use under high sample gas pressures, without significant risk that the membrane 24 in the channel 32 might leak or burst, with small, if any, high thermal conduction losses from the membrane 24 to its (silicon, polymer, or other material) support structure 42, thus maintaining a reduction of high thermal conduction losses to the environment via air under the membrane Also, the structure 31 may permit an integrated TCD 15 or 18 in the channel to be exposed to sample analyte peaks from its top and bottom surfaces thus providing about a two times factor increase in sensitivity over one detector surface exposure. The structure 31 may also facilitate an integration of thermal or electronic micro-pump or pumps 16.

The present three-wafer structure 31, illustrated in FIGS. 5a, 5b and 6, may provide the herein noted advantages at a reasonable fabrication cost despite a special bottom cap 41 fabrication and assembly of the heater mechanism and channel structure 31. There may be a sample gas flow under the membrane 24, in portion or space 46, which does not have a directly exposed stationary phase, for instance, a stationary phase 35. For clarity, the stationary phase or interactive element 35 is not shown in FIG. 5b. Openings, ports or cutouts 45 along the sides of membrane or support 24 may equalize the pressures at both broad surfaces of the membrane 24. A bottom cap 41 may provide a containment or sealing of the portion or space 46 from the environment external to the mechanism 31. Channel space 32 is likewise protected or sealed from the external environment. Due to the openings or ports 45, channel space 32 of one side of the membrane 24 and space 46 to the other side may share the same sample or analyte 11 being analyzed by the system 10. Examples of dimensions for the ports or openings 45 may include a 200 micron length and a 5 micron width. There may be about 20 microns of the membrane 24 between the openings 45 attached to an edge proximate to the wall of the chamber space 32. The 20 microns of membrane 24 may be regarded as a membrane support 69. There may be a support 69 between each port or opening 45.

The present structure 31 may be fabricated at the wafer level thereby keeping its cost low. The materials may include silicon, one or more of the polymers, and/or other materials. The structure may be fabricated with MEMS technology. The three wafers may include the top cap 30, a middle cap 42 for holding the membrane 24, and a bottom cap 41 for containing space 46. Loss in resolution of the present structure 31 with the stationary phase 35 on just one side of the membrane, if any, may be corrected by maintaining the same overall volumetric gas/liquid ratio and minimizing the space 46 under or proximate to the membrane 24. The adhesive used for wafer-to-wafer (W-W) bonding may be very fluid when melted and prone to leave the area it is intended to seal and bond. Instead, the W-W bond may be made with a more viscous material, such as a thin film of partially baked polymer (e.g., SU8 or the like), to provide a better and more elastic seal, and eliminate the liquid indium "adhesive" used in the previous structure from flowing away from the seal surface and/or plugging up (e.g., balling-up inside) the channel. The W-W bonds may be made with a material from a group consisting of viscous polymer, solder metal, and elements to form an anodic bond.

The structure 31 may provide exposure of both broad surfaces the membrane 24 to a sample 11. The structuring or etching a thin layer as the membrane 24 is possible because it is not subject to pressure stress due to the absence of a differential pressure between the two broad sides of the membrane 24. This thin membrane and support member 24 for the heaters and stationary phase (interactive elements) may provide the PHASED system 10 with excellent reliability, applicability, energy savings, integrated detector sensitivity and integratability with micro-pumps, along with an overall low fabrication cost.

In summary, the present structure 31 may provide PHASED system 10 improvements with wide applicability to high sample 11 pressures, low battery usage, compactness, sensitivity, portability, safety (IS certification), and other factors, for medical, industrial, environmental and governmental applications.

The present three-level or wafer PHASED structure 31 may withstand a sample gas pressure that is not limited by burst-pressure of its stationary phase-supporting membrane 24, enable low-energy operation of such membrane, and permit high performance of its detectors 15 and 18 situated in the channel 32. The high performance of the detectors may be due to their exposure at their top and bottom to analyte peaks.

The present structure 31 may involve the following characteristics. The use of an epoxy or polymer versus Si as the mechanism 31 structural material may reduce the dissipation rate of heat from the heated membrane 24 by a factor governed in part by the ratio of the thermal conductivities (TC) of Si/polymer which may be, for example, about 149/0.2=745. To prevent warping because of temperature changes, the channel material (e.g., SU-8 or equivalent) may be bonded to a silicon wafer. To "passivate" the organic channel material against adsorption of analyte, a very thin coating of an inert, non-catalytic and negligible adsorption capacity material 44 (e.g., Ni, Au, or the like) may be vacuum-deposited inside on the channel 32 walls via a conformal coating method. The material may also be deposited on the walls or inside surfaces of the space 46, which may be inside surfaces of wafers 41 and 42.

CNTs (carbon nanotubes) may be used as stationary phase material 35 on the inside of capillary of a fluid analyzer which may be like that of the present channel or space 32. Also, one may grow CNTs as interactive elements 35 inside of the channels of the PHASED pre-concentrator 21 and/or separator 23. A particular example of such material may be "treated" CNTs (possibly available from Lawrence Livermore National Labs) which can be tailored to GC needs.

The temperature coefficients of expansion (TCEs) and membrane strains for $Si_3N_4$ (which may be used), thermally grown $SiO_2$, and Si are respectively shown in a table herein. One may determine from this table that an intermediate membrane material may be advisable.

| Membrane Material | TCE ppm/° C. | Membrane Strain Baseline 500° C. Si-25° C.--SN-25° C. | Membrane Stain Baseline: 25° C. Si-25° C.--Mem-200° C. |
|---|---|---|---|
| $Si_3N_4$ | 3.5 | 25 | 200 |
| $SiO_2$ | <0.6 | 0 | −0.000613 |
| Si | 3.5 | −0.0013775 | −0.000105 |

Figure 7A:
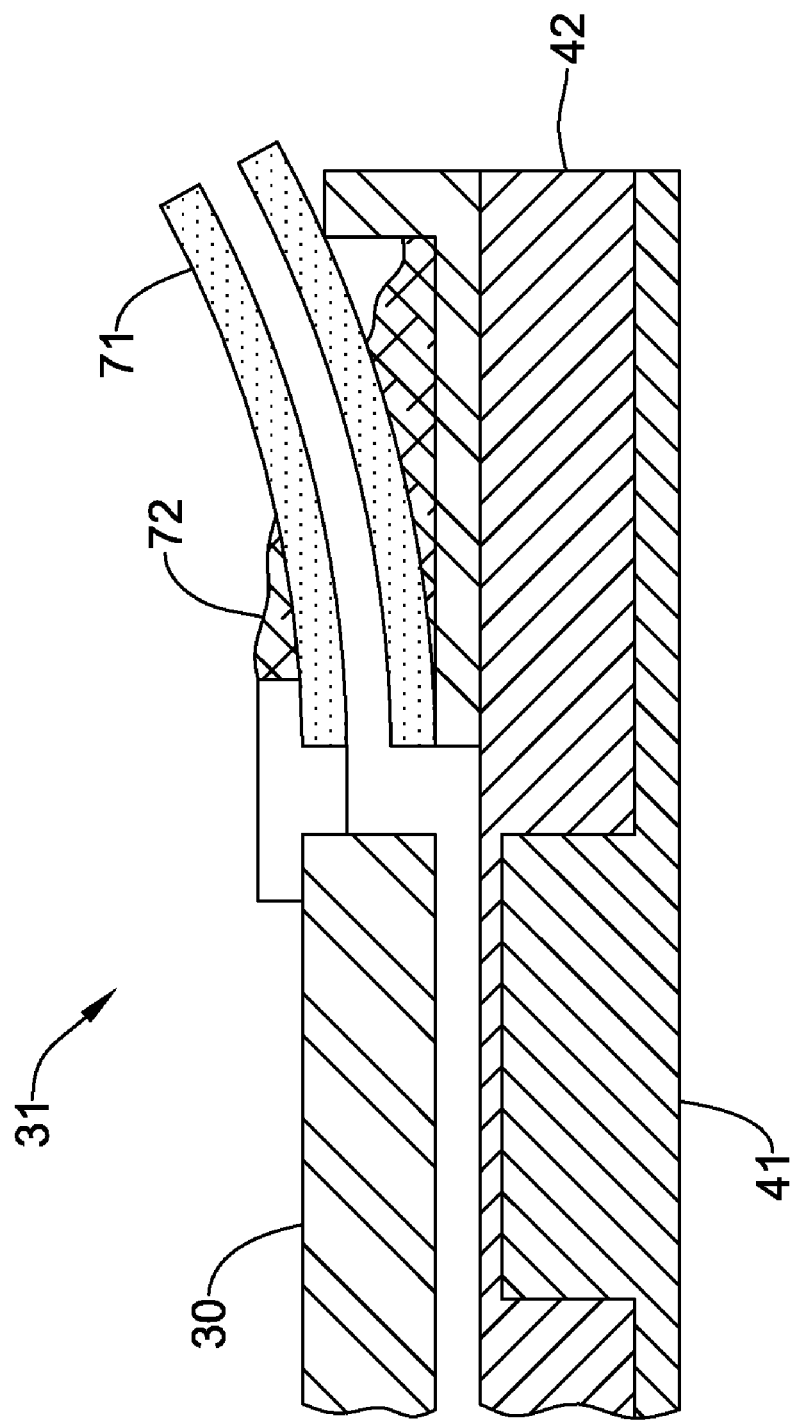
FIGS. 7a and 7b are cross-section and top views, respectively, of an illustrative example of a capillary attachment to a channel in the analyzer.
Figure 7B:
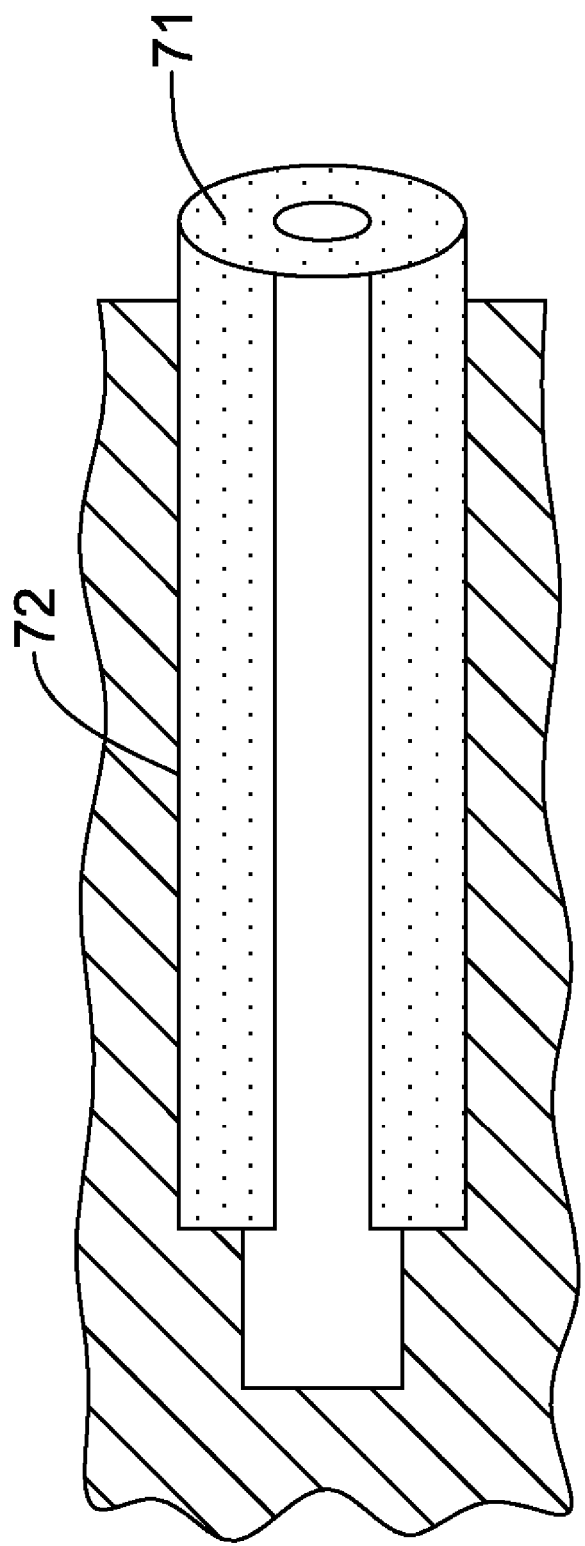

FIGS. 7a and 7b show a side cross-section view and a top view, respectively, of structure 31. The present wafer structure 31 may permit an attachment of capillaries 71 so that they go into and out of the PHASED chip at the inlet and the outlet with the respective capillary nearly parallel to rather than at right angles to the longitudinal dimension of the chip, as may be normally done, which can save space and provide compatibility with chip dicing of wafer in large scale production (so that no water and debris enter the PHASED channels in the production process). Each capillary 71 may be attached with an epoxy 72 to the wafer 30 or other appropriate structure piece. Shown in FIG. 7a is the bottom cap wafer 41, heater wafer 42 and the top cap wafer 30. FIG. 7b is a top view of the capillary 71 attachment with the epoxy 72.

Figure 8:
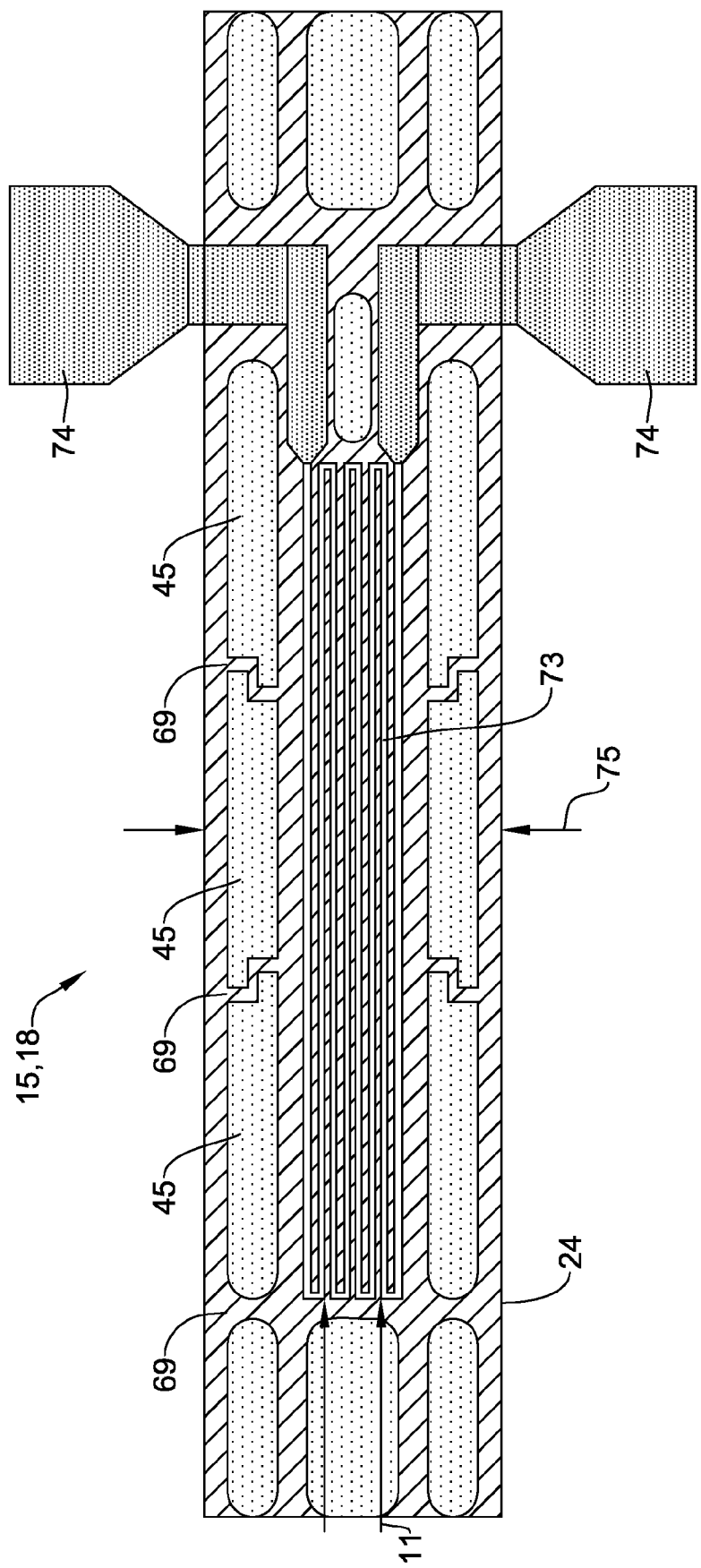
FIG. 8 is a top view of an illustrative example of a thermal conductivity detector situated in a channel of the analyzer.

FIG. 8 shows a layout of an illustrative example of a detector such as, for an illustrative example, a thermal conductivity detector (TCD) 15 or 18, which may be placed in the support member or membrane 24 of the present channel structure 31. A sample 11 may flow over and under a detector element 73. The location of detector 15, 18 may include channel structure 31 wall membrane supports 69 and gaps or openings 45 in the vicinity of channel space 32. Lead-outs 74 may provide electrical connection to the detector element 73. Dimension 75 of the detector may be about 100 microns. The port or gaps 45 in FIG. 5b appear aligned with the channel structure 31 wall of inside channel 32. In FIG. 8, with respect to the detector 15 or 18, the gaps 45 appear to be aligned several microns away from an alignment with the wall of channel or space 32. Various designs for detector placement may be implemented. The sensing element 73 may be situated on or exposed to both sides of the support member or membrane 24 for the increased sensitivity of the detector.

Polymer film-based sensors, in general, upon exposure to trace gases, may either change film resistivity, dielectric constant, strain and/or weight. Also, metal oxide films may change resistivity and serve as detector elements. The porous, spin-coatable materials may be used in GC pre-concentration and separation portions of the concentrator 21 and separator 23, respectively, of analyzer 10.

Also, polymer films may be used for gas detection in gas chromatography in the form of SAW detectors (surface acoustic wave, sensitive to changes in film mass). Useful detector results may be obtained with MPN (dodecanethiol monolayer protected gold nanoparticle) films, which change in electrical conductivity when exposed to different gases. These films may have excellent results when used as GC separator films in capillary columns or channels.

In the present specification, some of the matter may be of a hypothetical or prophetic nature although stated in another manner or tense.

Although the invention has been described with respect to at least one illustrative example, many variations and modifications will become apparent to those skilled in the art upon reading the present specification. It is therefore the intention that the appended claims be interpreted as broadly as possible in view of the prior art to include all such variations and modifications.

What is claimed is:

1. A channel structure for a fluid analyzer, comprising:
a first wafer;
a second wafer situated on the first wafer;
a membrane situated on the second wafer;
a third wafer situated on the membrane;
a stationary phase of the fluid analyzer situated on the membrane;
a first channel situated in the third wafer having an open side facing the stationary phase; and
a second channel situated in the first wafer having an open side facing the membrane.

2. The structure of claim 1, wherein at least one element of the structure comprising the first wafer, the second wafer, the third wafer and the membrane, comprises a material of lower thermal conductivity than silicon.

3. The structure of claim 1, wherein the membrane has openings between the first and second channels.

4. The structure of claim 3, further comprising:
a detector situated in the membrane; and
wherein the detector has a sensing area facing the first channel and facing the second channel.

5. The structure of claim 3, further comprising a heater situated in the membrane proximate to the stationary phase.

6. The structure of claim 5, wherein the openings in the membrane equalize the pressures in the first and second channels, and inhibit thermal conduction between the heated membrane and one or more walls of at least one channel.

7. A structure for a flow of a fluid for an analyzer, comprising:
a mid wafer having an opening situated along an elongated dimension of the mid wafer;
a support member situated proximate to the opening of the mid wafer and having an elongated dimension approximately parallel to the elongated dimension of the mid wafer;
a topcap wafer having a channel along an elongated dimension of the topcap wafer approximately parallel to the elongated dimension of the mid wafer, and the channel having an opening along the elongated dimension of the mid wafer and having the opening of the channel face the support member; and
a bottom cap wafer situated proximate to the mid wafer and covering a side of the opening of the mid wafer opposite of the side of the opening of the mid wafer facing the channel of the topcap wafer.

8. The structure of claim 7, wherein:
the support member is bonded to the mid wafer with a material from a group consisting of viscous polymer, solder metal, and elements to form an anodic bond;
the topcap wafer is bonded to the support member with a material from a group consisting of viscous polymer, solder metal, and elements to form an anodic bond; and
the bottom cap wafer is bonded to the mid wafer with a material from a group consisting of viscous polymer, solder metal, and elements to form an anodic bond.

9. The structure of claim 7, wherein:
the channel has an inlet and an outlet;
the inlet has a first capillary coupled to it; and
the outlet has a second capillary coupled to it.

10. The structure of claim 9, wherein:
the first capillary has one end coupled to the inlet of the channel with an epoxy; and
the second capillary has one end coupled to the outlet of the channel with an epoxy; and the first and second capillaries are coupled at the channel inlet and outlet, respectively, in a plane parallel to the elongated dimension of the channel.

11. The structure of claim 7, wherein the support element has at least one perforation between the channel of the topcap and the opening of the mid wafer.

12. The structure of claim 11, further comprising:
at least one heater element situated in the support member; and
at least one interactive element proximate to the heater element.

13. The structure of claim 12, wherein:
surfaces of the support member and the interactive element are exposable to a sample fluid; and
a detector in the support member may have an active sensing area proximate to a surface of the support member facing the opening between the channel of the topcap and proximate to a surface facing the opening of the mid wafer.

14. The structure of claim 12, wherein a thermal pump is integrated among the at least one heater element in the support member.

15. A channel for a fluid analyzer comprising:
a support wafer;
a first cap wafer situated on a first side of the support wafer to form a first channel; and
a second cap wafer situated on a second side of the support wafer to form a second channel; and
wherein the support wafer has at least one opening between the first channel and the second channel; and
further comprising:
at least one heater element situated in the support wafer; and
at least one interactive element proximate to the at least one heater element.

16. A channel for a fluid analyzer comprising:
a support wafer;
a first cap wafer situated on a first side of the support wafer to form a first channel; and
a second cap wafer situated on a second side of the support wafer to form a second channel; and
wherein the support wafer has at least one opening between the first channel and the second channel; and
further comprising:
a first capillary coupled to an inlet of the first channel;
a second capillary coupled to an outlet of the first channel; and
wherein the first and second capillaries are aligned approximately parallel to a line crossing the inlet and the outlet of the support wafer.

17. A channel for a fluid analyzer comprising:
a support wafer;
a first cap wafer situated on a first side of the support wafer to form a first channel; and
a second cap wafer situated on a second side of the support wafer to form a second channel; and
wherein the support wafer has at least one opening between the first channel and the second channel; and
further comprising:
at least one heater element situated in the support wafer;
at least one interactive element proximate to the at Least one heater element; and
a thermal pump, integrated into the first channel, comprising at least one heater element and valve.

18. A channel for a fluid analyzer comprising:
a support wafer;
a first cap wafer situated on a first side of the support wafer to form a first channel; and
a second cap wafer situated on a second side of the support wafer to form a second channel; and
wherein the support wafer has at least one opening between the first channel and the second channel; and
further comprising:
a detector situated in the support wafer; and
wherein the detector comprises an element having a sensing exposure on the first side and the second side of the support wafer.

* * * * *

UNITED STATES PATENT AND TRADEMARK OFFICE
CERTIFICATE OF CORRECTION

PATENT NO. : 7,578,167 B2
APPLICATION NO. : 11/383738
DATED : August 25, 2009
INVENTOR(S) : Bonne et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 361 days.

Signed and Sealed this

Seventh Day of September, 2010

David J. Kappos
*Director of the United States Patent and Trademark Office*